(12) United States Patent
Zhou et al.

(10) Patent No.: US 9,301,861 B2
(45) Date of Patent: Apr. 5, 2016

(54) STENT AND METHOD OF INSERTING A STENT INTO A DELIVERY CATHETER

(75) Inventors: Xiang Zhou, Oxfordshire (GB); Zhong You, Oxfordshire (GB); James Byrne, Oxfordshire (GB)

(73) Assignee: Isis Innovation Limited (GB)

( * ) Notice: Subject to any disclaimer, the term of this patent is extended or adjusted under 35 U.S.C. 154(b) by 0 days.

(21) Appl. No.: 14/343,522

(22) PCT Filed: Sep. 7, 2012

(86) PCT No.: PCT/GB2012/052215
§ 371 (c)(1),
(2), (4) Date: May 22, 2014

(87) PCT Pub. No.: WO2013/034930
PCT Pub. Date: Mar. 14, 2013

(65) Prior Publication Data
US 2015/0190256 A1   Jul. 9, 2015

(30) Foreign Application Priority Data
Sep. 9, 2011   (GB) .................................. 1115671.8

(51) Int. Cl.
*A61F 2/90*   (2013.01)
*A61F 2/91*   (2013.01)
(Continued)

(52) U.S. Cl.
CPC ... *A61F 2/90* (2013.01); *A61F 2/91* (2013.01); *A61F 2/915* (2013.01);
(Continued)

(58) Field of Classification Search
CPC ................ A61F 2/91; A61F 2/82; A61F 2/89

USPC ................................................... 623/1.15–1.4
See application file for complete search history.

(56) References Cited

U.S. PATENT DOCUMENTS

| 6,860,900 B2 * | 3/2005 | Clerc et al. .................. 623/1.35 |
| 2003/0109917 A1 * | 6/2003 | Rudin et al. ................. 623/1.15 |

(Continued)

FOREIGN PATENT DOCUMENTS

| CA | 2214627 | 9/1998 |
| CN | 2322571 | 6/1999 |

(Continued)

OTHER PUBLICATIONS

PCT; International Search Report and Written Opinion dated Jun. 12, 2013 in Application No. PCT/GB2012/052215.
(Continued)

*Primary Examiner* — Suzette J Gherbi
(74) *Attorney, Agent, or Firm* — Snell & Wilmer L.L.P.

(57) ABSTRACT

Stents and method of inserting a stent into a delivery catheter are disclosed. In a disclosed embodiment, a stent for redirecting blood flow away from an aneurysmal sac is provided. The stent comprises an elongate frame (2) that is radially contractable from a fully radially expanded state to a radially contracted state in a process involving elongation of the frame, wherein: the fully radially expanded state represents the state of the frame at body temperature when no external force is applied to the frame; in the radially contracted state the frame has a maximum lateral dimension that is at least 30% smaller than the maximum lateral dimension of the frame in the fully radially expanded state; and the frame comprises a low porosity region (4) for positioning at the opening to the aneurysmal sac, the low porosity region having a porosity of less than 50% when the frame is in the fully radially expanded state.

16 Claims, 10 Drawing Sheets

(51) Int. Cl.
*A61F 2/915* (2013.01)
*A61F 2/82* (2013.01)
*A61F 2/95* (2013.01)

(52) U.S. Cl.
CPC .. *A61F 2002/823* (2013.01); *A61F 2002/9522* (2013.01); *A61F 2210/0014* (2013.01); *A61F 2230/0054* (2013.01); *A61F 2250/0023* (2013.01)

(56) References Cited

U.S. PATENT DOCUMENTS

| | | | |
|---|---|---|---|
| 2003/0149464 A1 | 8/2003 | Dong | |
| 2004/0133266 A1* | 7/2004 | Clerc et al. | 623/1.22 |
| 2005/0283220 A1 | 12/2005 | Gobran | |
| 2006/0030926 A1* | 2/2006 | Berra | 623/1.13 |
| 2007/0016283 A1* | 1/2007 | Greenhalgh et al. | 623/1.15 |
| 2007/0021816 A1* | 1/2007 | Rudin | 623/1.4 |
| 2007/0129786 A1 | 6/2007 | Beach et al. | |
| 2007/0239261 A1* | 10/2007 | Bose et al. | 623/1.15 |
| 2009/0082848 A1 | 3/2009 | Mori et al. | |
| 2009/0248132 A1 | 10/2009 | Bloom et al. | |
| 2011/0054589 A1* | 3/2011 | Bashiri et al. | 623/1.15 |
| 2012/0296361 A1* | 11/2012 | Cam et al. | 606/191 |
| 2013/0123901 A1* | 5/2013 | Connor et al. | 623/1.15 |
| 2015/0032202 A1* | 1/2015 | Tanweer et al. | 623/1.42 |

FOREIGN PATENT DOCUMENTS

| | | |
|---|---|---|
| CN | 101415380 | 4/2009 |
| DE | 102007061931 | 6/2009 |
| WO | 9709945 | 3/1997 |
| WO | 9940873 | 8/1999 |
| WO | 0182835 | 8/2001 |
| WO | 2006034114 | 3/2006 |
| WO | 2007117645 | 10/2007 |
| WO | 2010120926 | 10/2010 |
| WO | 2013034930 | 3/2013 |

OTHER PUBLICATIONS

Fischell et al., "Handbook of Coronary Stents," Fourth Edition, Netherlands Heart Journal, 40-48, 176-186, 214-226, (2002).

* cited by examiner

STENT AND METHOD OF INSERTING A STENT INTO A DELIVERY CATHETER

CROSS-REFERENCE TO RELATED APPLICATIONS

The present application is a U.S. National Stage entry under 35 U.S.C. §371 of International Application No. PCT/GB2012/052215, filed on Sep. 7, 2012, which claims the benefit of United Kingdom application 1115671.8, filed on Sep. 9, 2011.

The present invention relates to the field of stents for use in treating aneurysms, for example intracranial aneurysms (also known as cerebral aneurysms).

An intracranial aneurysm is a weak region in the wall of an artery in the brain, where dilation or ballooning of the arterial wall may occur. Histologically, decreases in the tunica media, the middle muscular layer of the artery, and the internal elastic lamina cause structural defects. These defects, combined with hemodynamic factors, lead to aneurismal out-pouchings. Intracranial aneurysms are quite common diseases with a prevalence ranging from one to five percent among adult population according to autopsy studies. In the US alone, ten to twelve million people may have intracranial aneurysms.

Current methods for treating intracranial aneurysms include surgical clipping and endovascular coiling. In the surgical clipping method, the skull of the patient is opened, and a surgical clip is placed across the neck of the aneurysm to stop blood from flowing into the aneurysm sac. The risk of this method is relatively high, especially for elderly or medically complicated patients. Endovascular coiling procedure is a less invasive method involving placement of one or more coils, delivered through a catheter, into the aneurysm until the sac of the aneurysm is completely packed with coils. It helps to trigger a thrombus inside the aneurysm. Although endovascular coiling is deemed to be safer than surgical clipping, it has its own limitations. First, after the aneurysm is filled with the coils, it will remain its original size. As a result, the pressure on the surrounding tissue exerted by the aneurysm will not be removed. Second, this procedure is effective for the aneurysm that involves a well-formed sac with a small neck. When used to treat the wide-neck aneurysm, the coil is likely to protrude into the parent vessels. A solution to prevent coil protrusion is to use a stent in combination with coiling embolization. In the stent-assisted coiling procedure, a stent is first placed across the aneurysm neck, serving as a scaffold inside the lumen. Then, the coils are delivered into the sac of the aneurysm through the interstices of the stent. Although this method can solve some problems of purely coiling, it still has some drawbacks. First, a microcatheter through which the coils are sent into the aneurysm sac has to be navigated through the interstices of the stent. This process is difficult and time-consuming. Second, the coils are still used to fill the sac of the aneurysm. As a result, the aneurysm size remains the same after the treatment. Furthermore, when it comes to the pseudoaneurysm where no fully-formed aneurysm sac can be identified, coiling methods are not applicable.

Using a stent alone to treat the aneurysm is a promising way to avoid the problems stated above. In this method, a stent with an area of coverage is placed across the aneurysm neck, blocking it sufficiently to restrain blood from flowing into the sac and finally to trigger a thrombus within the aneurysm. Because the aneurysm solidifies naturally on itself, there is no danger of its rupture. Furthermore, because no coil is involved in this method, the aneurysm will gradually shrink as the thrombus is absorbed. Consequently, the pressure applied on the surrounding tissue can be removed. The reason why this method has not used is because of the difficulty in designing the stent. It has to be flexible enough to pass through and morph to the very tortuous blood vessels in the brain while at the same time providing sufficient coverage to shut the aneurysm. Current stents made for the stent-assisted coiling, such as Neuroform stent (Boston Scientific), LEO stent (Balt) and Enterprise stent (Corids), have a very open design to allow the coils to pass through the interstices. They do not provide much coverage at all. Therefore, they are inadequate for direct treatment of the aneurysm. PED (ev3) and SILK stent (Balt) are currently two dedicated flow diverters under clinical trials. However, they have their own limitations mainly because both stents are braided stents, which do not provide much radial strength. Besides, use of these stents may cause blockage of branch blood vessels.

It is an object of the invention to at least partially address one or more of the shortcomings described above in relation to the prior art.

According to an aspect of the invention, there is provided a stent for redirecting blood flow away from an aneurysmal sac, comprising: an elongate frame that is radially contractable from a fully radially expanded state to a radially contracted state in a process involving elongation of the frame, wherein: the fully radially expanded state represents the state of the frame at body temperature when no external force is applied to the frame; in the radially contracted state the frame has a maximum lateral dimension that is at least 30% smaller than the maximum lateral dimension of the frame in the fully radially expanded state; and the frame comprises a low porosity region for positioning at the opening to the aneurysmal sac, the low porosity region having a porosity of less than 50% when the frame is in the fully radially expanded state.

As compared to surgical clipping, the presently disclosed stent is for use in the minimum invasive method which is much safer, has less mobility and mortality rate, requires less hospital stay and reduces the overall treatment cost. As compared to other minimum invasive methods, e.g. coiling embolization or stent-assisted coiling, the presently disclosed stent does not involve coils, which leads to several advantages, e.g. the mass effect of the aneurysm is reduced, and the stent is suitable for treating both saccular and fusiform aneurysms. As compared to current flow-diverters (i.e. stents configured to divert flow away from an aneurysmal sac), e.g. PED (ev3) and SILK stent (Balt), the presently disclosed stent can provide higher radial strength and tailored surface coverage which is useful to prevent the blockage of branch blood vessels.

The provision of a frame that elongates to a substantial degree as part of the radial contraction allows a high degree of radial contraction even when the frame is configured to present a low porosity in the expanded state. It is therefore possible to provide a frame that can be inserted into delivery catheters of very small diameter, for example less than 5 mm diameter, or more preferably less than 3 mm diameter. This property expands the range of clinical uses that are available.

Preferably, the frame is laser cut from a cylindrical tube in a single piece. The frame can thus be manufactured easily. The structural simplicity and/or lack of material interfaces promotes reliability.

The frame may be configured so that all elements of the frame stay at a common radius for all degrees of radial contraction. No elements of the frame are made to overlap in the radial direction during radial contraction. There is thus no danger of friction between radially overlapping elements, for example during implantation of the frame, which may require a degree of flexing to navigate tortuous regions of vasculature. The outer surface can be made smoother in the radially contracted state in comparison to systems which require elements to overlap radially in the radially contracted state, which facilitates insertion of the frame into a delivery catheter.

Preferably the frame is formed from Nitinol or stainless steel.

According to an aspect, there is provided a method of inserting a stent into a delivery catheter, wherein: the stent comprises an elongate frame that is radially contractable from a fully radially expanded state to a radially contracted state in a process involving elongation of the frame, the frame comprising a low porosity region having a porosity of less than 50% when the frame is in the fully radially expanded state, the method comprising: cooling the stent to a temperature at which deformation of the frame is predominantly plastic; elongating the frame longitudinally and compressing the frame radially so that the frame is in the radially contracted state; and inserting the frame into the delivery catheter.

Inserting the stent while it is in the plastic state makes it possible to carry out the radial contraction and insertion steps separately, which improves reliability and efficiency.

According to an aspect, there is provided a method of inserting a stent into a delivery catheter, wherein: the stent comprises an elongate frame that is radially contractable from a fully radially expanded state to a radially contracted state in a process involving elongation of the frame, the frame comprising a low porosity region having a porosity of less than 50% when the frame is in the fully radially expanded state, the method comprising: longitudinally constraining one end of the frame; inserting a longitudinally rigid element through the frame, from said one end of the frame; establishing engagement between the rigid element and the frame at one or more anchoring points at the other end of the frame; pushing the rigid element longitudinally through the frame so that the frame elongates; radially contracting the frame; and inserting the frame into the delivery catheter.

This disclosed method allows the radial contraction process to be achieved using a simple pushing action, even when the stent is in an elastic state (e.g. where a Nitinol frame at body temperature is used). This method facilitates reliable and efficient insertion without the need for cooling of the stent.

Embodiments of the invention will now be described, by way of example only, with reference to the accompanying drawings in which corresponding reference symbols indicate corresponding parts, and in which.

In the discussion below, any reference to an element being deformable is understood to encompass both positive deformation (e.g. elongation, extension) and negative deformation (e.g. contraction). Typically, the stent will be formed from a material that is elastic at room temperature and/or at body temperature. Typically, the stent will be configured so that all deformations of the stent frame during normal use at room temperature and/or body temperature will be elastic. However, this is not essential. The stent frame may be configured to allow a certain degree of plastic deformation at room temperature and/or body temperature.

Figure 1:
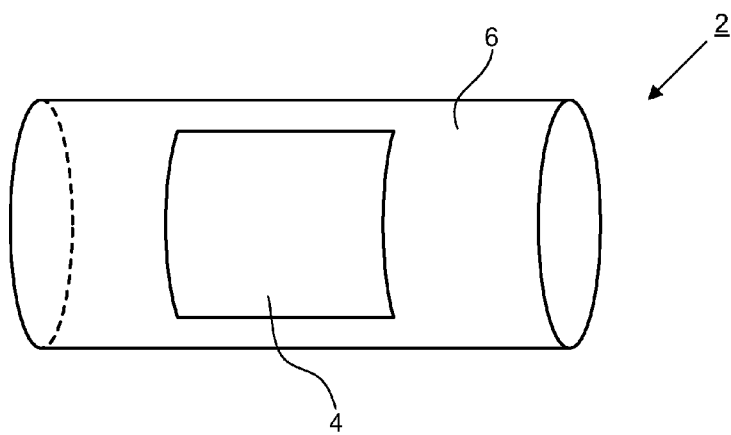
FIG. 1 is a schematic side view of a stent in a fully radially expanded state, showing a low porosity region and a higher porosity region.
Figure 2:
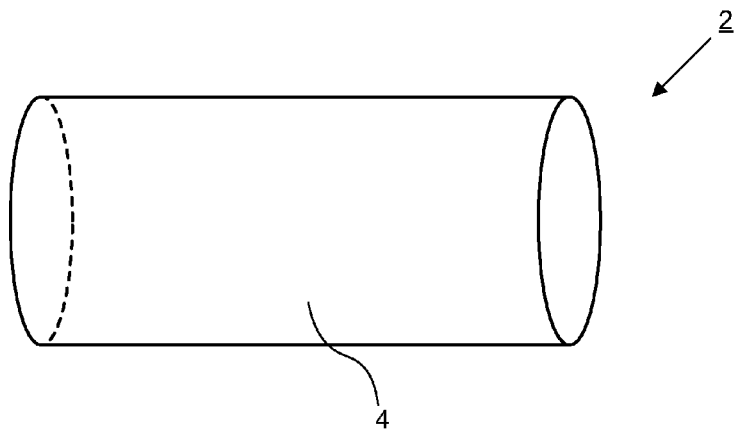
FIG. 2 is a schematic side view of a stent in a fully radially expanded state that has a low porosity region extending around the whole circumference of the stent for at least a portion of the length of the stent.

FIGS. 1 and 2 are schematic side views of an example stent in a fully radially expanded state. The stent comprises an elongate frame 2. The frame 2 may be cylindrical for example. When the frame 2 is cylindrical, the maximum lateral dimension is the same at all positions and angles (i.e. it is equal to the diameter). When the frame 2 is not cylindrical the maximum lateral dimension may be different at different positions and/or angles. The maximum lateral dimension defines the minimum interior diameter of a cylindrical tube (e.g. a delivery catheter) that the frame could be inserted into.

Figure 3:
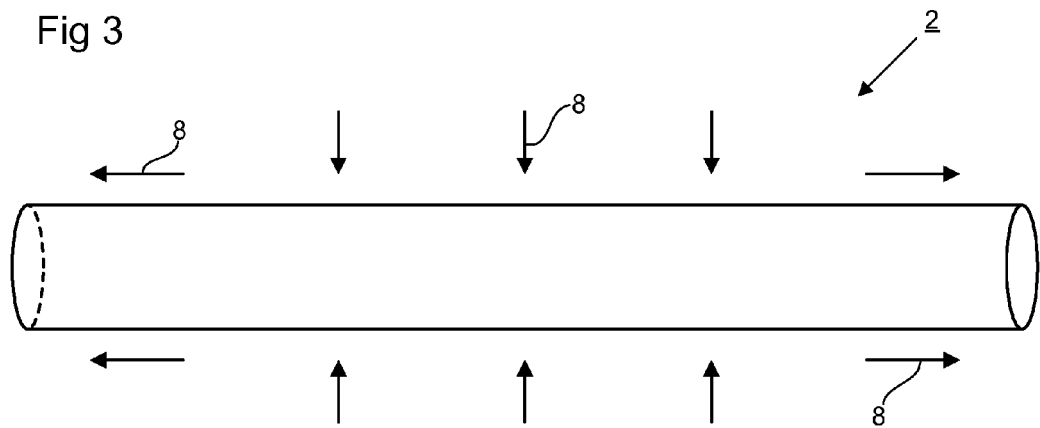
FIG. 3 is a schematic side view of the stent of FIG. 2 in a radially contracted state for insertion into a delivery catheter.

The frame 2 is configured such that the maximum lateral dimension of the frame can be reduced by elongating the frame longitudinally from the fully radially expanded state to a radially contracted state. This process is illustrated schematically in FIG. 3 for the frame 2 of FIG. 2. Arrows 8 illustrate schematically the longitudinal extension and radially contraction. In the radially contracted state the frame 2 is substantially narrower than in the fully radially expanded state. Preferably the maximum lateral dimension is 30% smaller in the radially contracted state, more preferably 50% smaller. Radially contracting the frame 2 allows the frame to be inserted into a narrower delivery catheter for deployment at the site of interest. It is generally desirable for the delivery catheter to be as narrow as possible. This is particularly the case where access to a deployment site requires navigation of tortuous regions of vasculature. This may often be the case, for example, when treating a cerebral aneurysm.

The fully radially expanded state represents the configuration of the frame 2 at body temperature when no external force is applied to the frame 2. This state may therefore be referred to as the "relaxed" or "free" state. Reference is made to the temperature because the frame may be made of material, such as Nitinol, that is elastic at body temperature but plastic at other temperatures, for example at very low temperatures. In the plastic state, the frame 2 may be made to stay in a plastically deformed state of a different radius without any external force being applied to it. However, when the frame 2 returns to body temperature the frame 2 may become elastic again and return to the expected radius associated with the fully radially expanded state.

In the discussion below it is understood that the term porosity, p, refers to the ratio of the surface area of open regions to the total external surface area occupied by the frame or portion of frame that is being described. The total external surface area is the sum of the surface area of the open regions and the surface area of the regions occupied by the material of the frame. When the frame is cylindrical, the total external surface area is simply $2\pi.R.L$, where R is the radius of the cylinder and L is the length of the cylinder.

The frame 2 comprises a low porosity region 4 for spanning the opening (also referred to as the "neck") to an aneurysmal sac. The low porosity region 4 has a porosity of less than 50% when the frame is in the fully radially expanded state. The frame 2 is preferably configured so that the maximum radius in the fully radially expanded state is close to, preferably slightly greater than, for example 10% greater than, the nominal radius of the blood vessel (e.g. the radius that the blood vessel would have in the absence of the aneurysmal sac, or the radius of the blood vessel in the region of the blood vessel immediately outside of the opening to the aneurysmal sac). Configuring the low porosity region 4 to have a porosity of less than 50% when the frame 2 is in the fully radially expanded state ensures that the porosity of the portion of the frame 2 that spans the opening to the sac when the stent is deployed is less than 50%. A porosity of less than 50% will inhibit the flow of blood into the aneurysmal sac to an extent that should promote blood clotting in most cases. Preferably, the porosity of the low porosity region when the frame 2 is in the fully radially expanded state is less than 40%, more preferably less than 30%, more preferably less than 20%. Making the porosity lower increases the extent to which blood flow is diverted away from the sac and further encourages blood clotting within the sac.

In the embodiment of FIG. 1, the low porosity region 4 is surrounded by a higher porosity region 6, both longitudinally and circumferentially. In such a configuration, the frame 2 would have to be oriented correctly (both longitudinally and azimuthally) when deployed so that the low porosity region 4 is placed over the opening to the sac. FIG. 2 illustrates an alternative configuration where the low porosity region 4 expands all the way around the circumference of the frame 2 and along all or a portion of the length of the frame 2. The arrangement of FIG. 2 may be easier to deploy because it is no longer necessary to consider the azimuthal alignment of the stent. In addition, the position of the stent longitudinally does not need to be controlled as accurately because the low porosity region 4 expands further longitudinally. However, expanding the low porosity region 4 in this way may lead to the frame 2 having to be stiffer because more material will be required to provide the larger low porosity region. A stiffer frame 2 may be more likely to cause damage or irritation to the patient. In addition, an expanded region of low porosity may act to divert blood flow away from openings other than the opening to the sac, for example openings to branch vessels, which is undesirable.

In other embodiments, the size and shape of the low porosity region 2 may be configured differently. For example, the porosity may be configured to vary more gradually, rather than suddenly changing at the boundary of the low porosity region. Such gradual changes may reduce the likelihood of damage or irritation to tissue. In the arrangement of FIG. 1, the low porosity region 4 is bounded by higher porosity regions in both longitudinal directions, and circumferentially. In alternative embodiments, the low porosity region may be bounded on only one longitudinal side by a higher porosity region. Additionally or alternatively, the low porosity region may expand all the way around the circumference in a closed loop.

Consider a stent with a porosity $\rho$ in the fully radially expanded state. If the radius and length of the frame in the fully radially expanded state are $R_0$ and $L_0$, respectively, the minimum radius $R_{min}$ that the frame 2 can achieve in the radially contracted state, defined by the state in which the porosity becomes zero, is governed by $$R_{min} = \frac{(1-\rho)L_0}{L_1} \cdot R_0$$

where $L_1$ is the length of the frame in the radially contracted state. This relationship assumes that elements of the frame are not allowed to overlap with each other in the radial direction.

This relationship illustrates that if the length of the frame is not allowed to change to any significant extent, the radius can only reduce by a factor of $\rho$. As $\rho$ needs to be quite low (less than 50% in the low porosity region), this represents a significant limitation to the extent to which the stent can be narrowed for insertion into a delivery catheter. For example, if the porosity $\rho$ of the frame is 20% and the length of the frame is not allowed to change during radial contraction, i.e. $L_1=L_0$, the frame can achieve only a maximum 20% reduction in radius. The provision of a frame that can expand longitudinally when adopting the radially contracted state is based on this understanding and allows much greater reductions in radius to be achieved. For example, if the length is allowed to double, i.e. $L_1=2.L_0$, the frame can achieve a 60% reduction in radius for a porosity of 20%.

Preferably, the frame is configured so that it can be elongated by at least 25%, more preferably by at least 50%, even more preferably by 100% or 150%.

Figure 4:
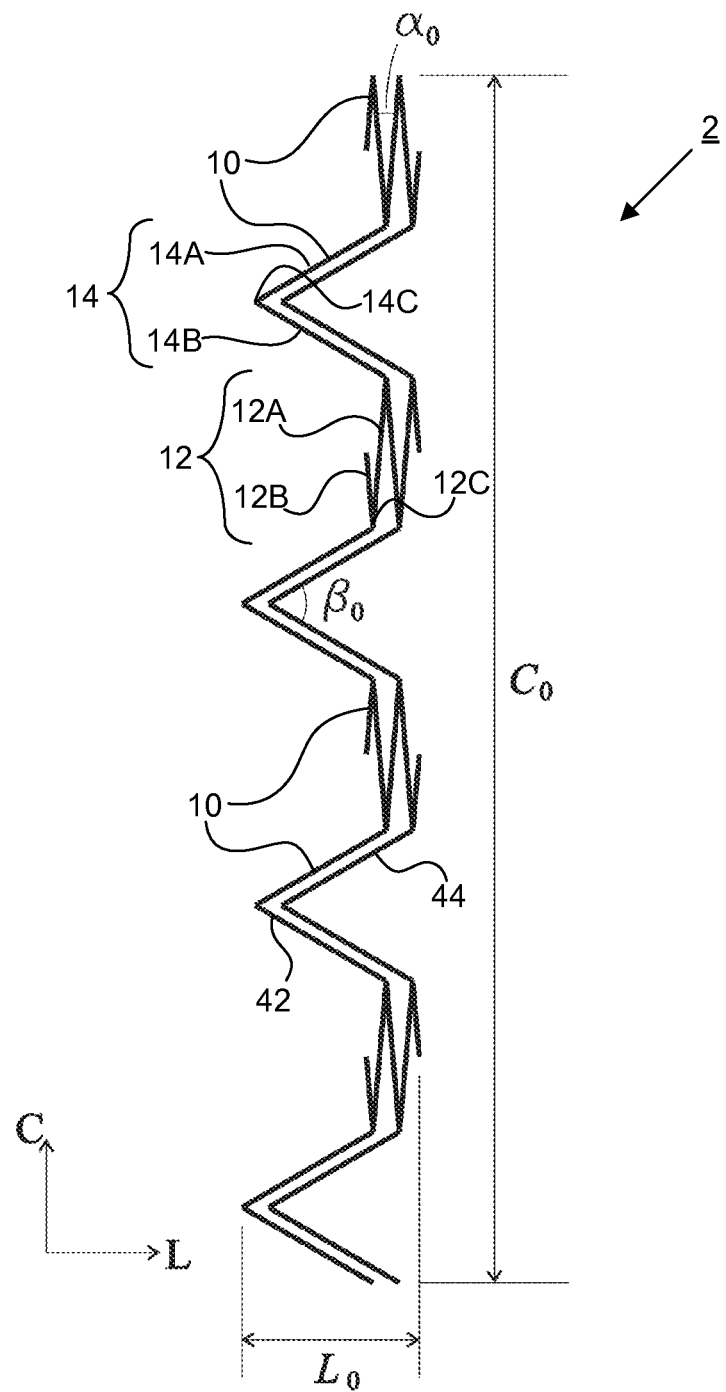
FIG. 4 is a schematic unfolded view of a network of interconnecting arms which when folded into a cylinder would form a portion of a stent in the fully radially expanded state.

FIG. 4 is a schematic plan view of a portion of an example frame 2, in the fully radially expanded state, notionally unwrapped from its actual cylindrical or tubular shape into a flat shape, where $L_0$ is the longitudinal length and $C_0$ is the circumference.

The frame 2 comprises a network of interconnecting arms 10. In this embodiment, the interconnecting arms 10 form a plurality of longitudinally deformable elements 12 and a plurality of circumferentially deformable elements 14. In this embodiment, each longitudinally deformable element 12 consists of two arms 12A and 12B that are connected together at an elbow 12C. The angle at the elbow 12C is labelled $\alpha_0$. In this embodiment, each circumferentially deformable element 14 consists of two arms 14A and 14B connected together at an elbow 14C. The angle at the elbow 14C is labelled $\beta_0$. In this embodiment, a smaller $\alpha_0$ can lead to lower porosity and higher longitudinal flexibility.

Folding of the frame 2 can be divided into two steps: a longitudinal extension and a radial contraction. The steps can be carried out one after the other or at the same time. If the steps are carried out at the same time, the longitudinal extension must progress sufficiently quickly relative to the radial contraction that any circumferentially deformable elements that overlap in the longitudinal direction initially are displaced longitudinally by a sufficient distance that they do not come into contact prematurely in the circumferential direction and block the radial contraction.

Figure 5:
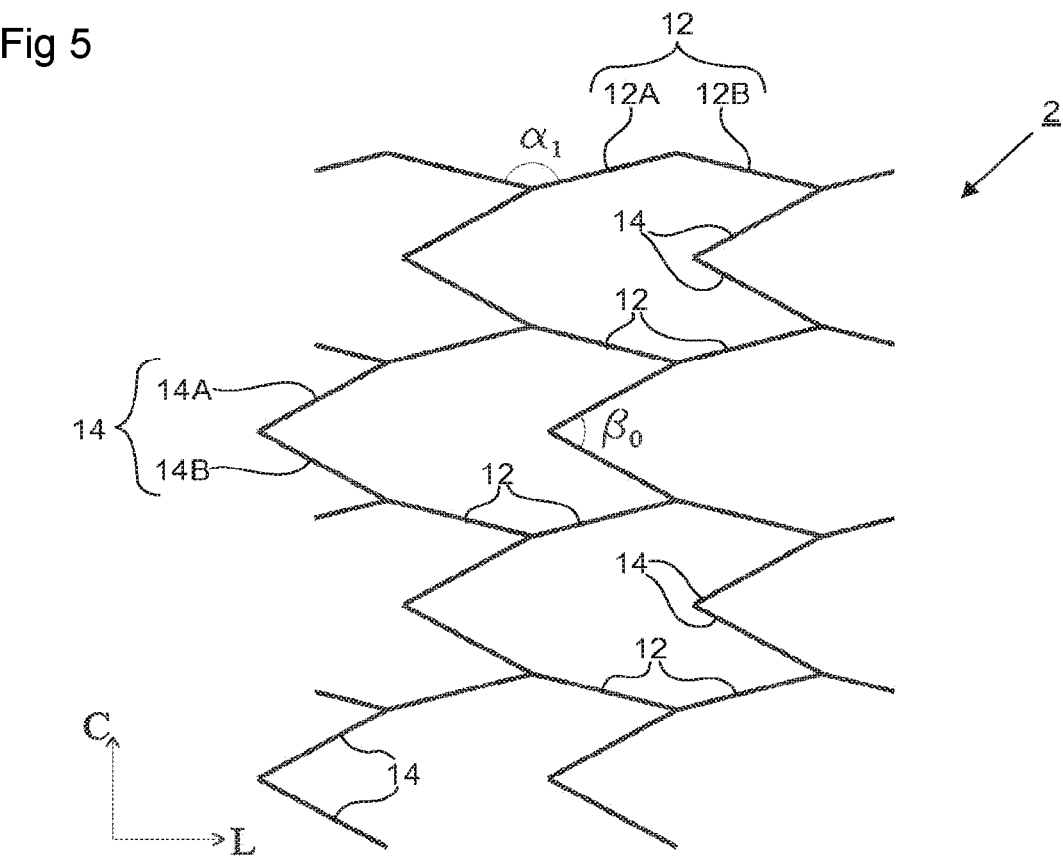
FIG. 5 is a schematic unfolded view of the network of FIG. 4 after extension in the longitudinal direction.

The state of the frame 2 after a longitudinal extension (but no radial contraction) is illustrated schematically in FIG. 5. The extension along L is accommodated by an increase in the angle at the elbows 12C of the longitudinally deformable elements from $\alpha_0$ to $\alpha_1$, where $\alpha_1$ can in general be any value larger than $\alpha_0$.

Figure 6:
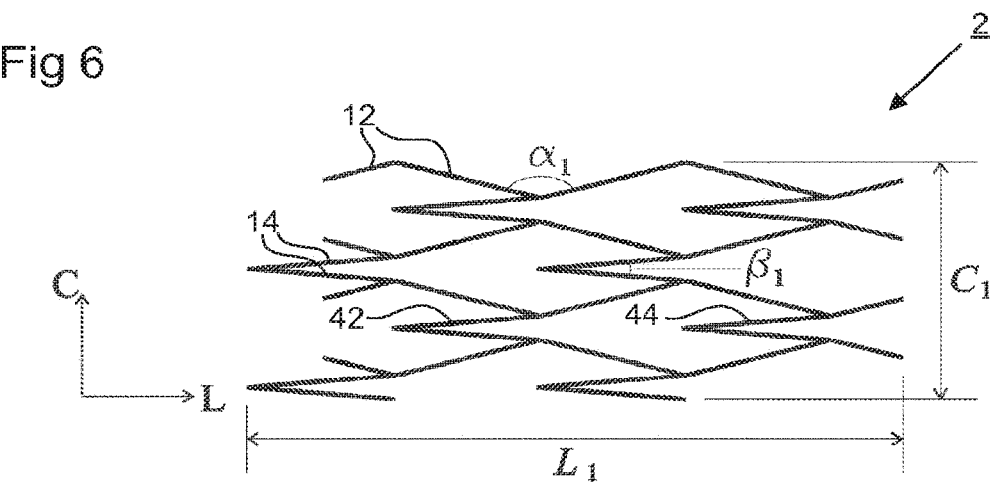
FIG. 6 is a schematic unfolded view of the network of FIG. 5 after compression in the circumferential direction, the network of interconnecting arms being such as to form a stent in the radially contracted state when folded to form a cylinder.

The state of the frame 2 after a subsequent radial contraction is illustrated schematically in FIG. 6. The radial contraction (corresponding to a reduction in the length of the unfolded frame 2 along the C direction) is accommodated by a reduction in the angle at the elbows 14C of the circumferentially deformable elements 14 from $\beta_0$ to $\beta_1$, where $\beta_1$ can in general be any value smaller than $\beta_0$, and $L_1$ and $C_1$ are the length and circumference of the radially contracted frame 2, respectively. When folded into a cylinder, the frame layout in FIG. 6 represents an example of a frame in the radially contracted state, suitable for insertion into a delivery catheter for example. Optionally, the frame 2 could be contracted further until the angle $\beta_1$ becomes as close to zero as is possible without causing buckling/damage to the elbows 14C.

In embodiments, the longitudinally deformable elements 12 may be connected to the circumferentially deformable elements 14 in such a way that longitudinal extension of the longitudinally deformable elements 12 causes longitudinal displacement of the circumferentially deformable elements with which they are in contact (with or without deformation of the circumferentially deformable elements 14). This functionality can be seen to occur in the embodiment of FIGS. 4 to 6. Neighbouring "V-shaped" circumferentially deformable elements 14 can be seen to be driven further apart by extension of the longitudinally deformable elements 12 (see transition from FIG. 4 to FIG. 5).

If a first one of the circumferentially deformable elements 14 has a portion that is bounded on one or both sides in the circumferential direction by a portion of a second circumferentially deformable element 14 when the frame 2 is in the fully radially expanded state, there is a risk that these two circumferentially deformable elements 14 could be driven into contact with each other circumferentially during radial contraction, thus blocking the radial contraction. The elongation should therefore progress so as to avoid this. This may be achieved by coupling the circumferentially deformable elements 14 to the longitudinally deformable elements 12 in such a way that the circumferentially deformable elements 14 are driven apart during the elongation by a sufficient amount to remove any longitudinal overlap (i.e. so that no portion of one circumferentially deformable element 14 is bounded on either side in the circumferential direction by any portion of a neighbouring circumferentially deformable elements 14) by the time the radially contracted state is reached. This functionality is illustrated schematically in FIGS. 4 and 6. In FIG. 4 it can be seen that most of the circumferentially deformable element 44 (i.e. all of it except for two small regions at the ends of the arms furthest from the elbow of the element 44) is bounded on both sides in the circumferential direction by circumferentially deformable element 42. However, when the radially contracted state is reached in FIG. 6 it can be seen that the two circumferentially deformable elements 42 and 44 have been driven apart longitudinally so that there is no longer any overlap between them (no part of either element lies at the same longitudinal position as any part of the other element).

In the embodiment of FIGS. 4 to 6, the longitudinally deformable elements 12 can be expanded or contracted without any corresponding circumferential contraction or extension of the circumferentially deformable elements 14. In such embodiments, the circumferentially deformable elements 14 may be displaced without any change in the shape of the circumferentially deformable elements (the extension of the frame being provided entirely by deformation of the longitudinally deformable elements). However, this is not the case in other embodiments. In other embodiments, the circumferentially deformable elements may be configured to contract radially when the longitudinally deformable elements are extended and vice versa This is the case in the embodiment of FIGS. 9 and 10 for example.

Similarly, the circumferentially deformable elements may be configured so that they can contract or expand to a degree without any corresponding extension or contraction of the longitudinally deformable elements. This is the case in the embodiment of FIGS. 4 to 6, for example, where the circumferential contraction is possible up until longitudinally neighbouring circumferentially deformable elements come into contact. The degree of movement could be increased by increasing the separation between the circumferentially deformable elements 14, but this would tend to increase the porosity of the frame 2 in the fully radially expanded state.

In general, longitudinal extension will involve a degree of circumferential contraction of the longitudinally deformable elements. However, where separate circumferentially deformable elements are provided, as in the embodiments of FIGS. 4 to 8, in switching from the fully radially expanded state to a radially contracted state suitable for inserting the stent into a delivery catheter, the majority of the circumferential contraction will generally be provided by the circumferentially deformable elements. Where no separate circumferentially deformable elements are provided, as in the embodiments of FIGS. 9 to 13, all (or the majority, for example greater than 90%) of the circumferential contraction will be provided by the longitudinally deformable elements (which may simply be referred to as "deformable elements" in this case).

Figure 7:
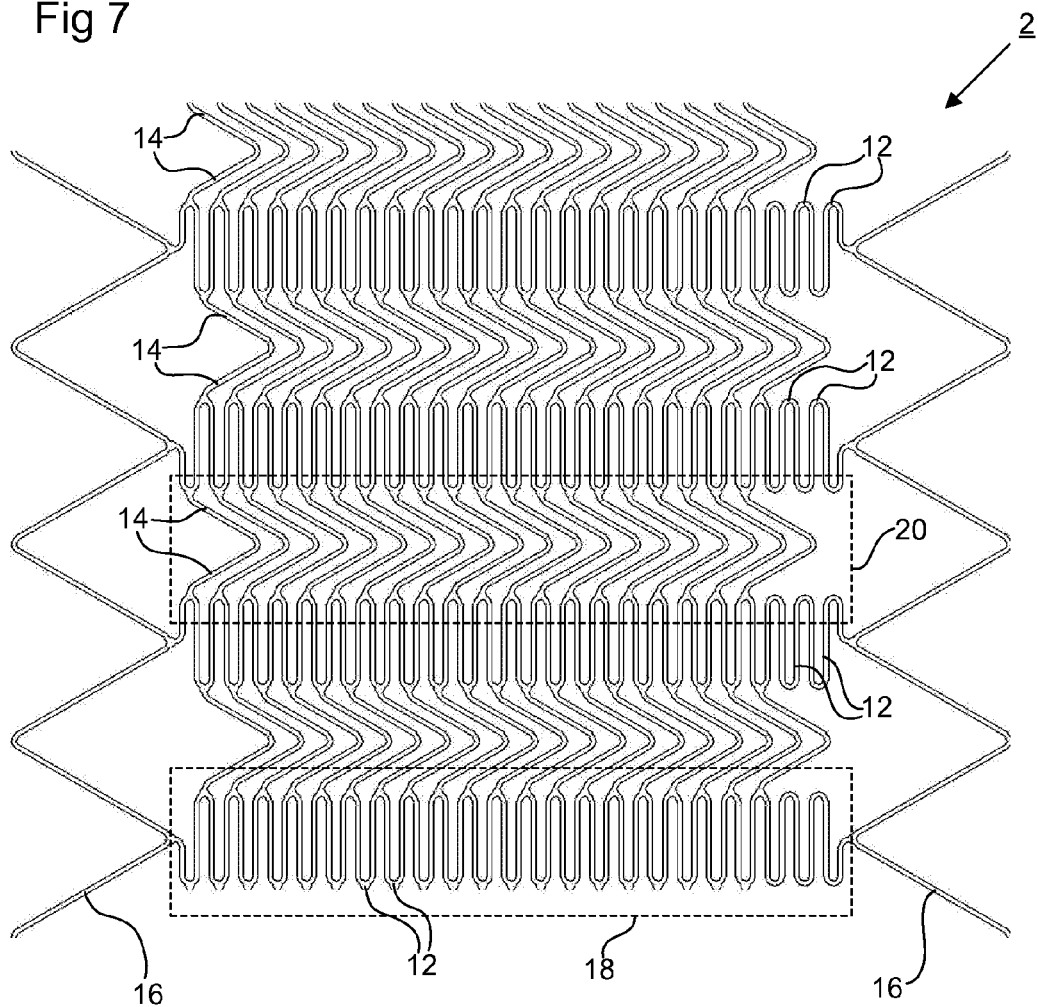
FIG. 7 is a schematic unfolded view of an alternative network of interconnecting arms comprising four sets of longitudinally deformable elements connected directly to each other and aligned to form four longitudinally periodic structures.

The basic form shown in FIGS. 4 to 6 (or other basic forms) can be repeated in the longitudinal direction L to form a longer frame 2. FIG. 7 shows an example of a longer frame 2 consisting of 10 repeating basic forms of the type shown in FIGS. 4 to 6 (although the elbows have been made more rounded, which may be desirable to avoid stresses in the frame 2, and to avoid the presence of sharp elements that may cause irritation or damage to tissue). FIG. 7 also shows an example of how to design the ends 16 of the frame 2. In this example, a zigzag ring 16 is connected to each end of the frame 2.

In the embodiment of FIG. 7, four sets of longitudinally deformable elements 12 are present, each set comprising a plurality of elements 12 connected together so as to act in series. The broken-line box 18 contains elements 12 in one of the four sets. The elements 12 in each set are also aligned with each other in a direction parallel to the axis of the frame 2. In the example shown, the elements 12 in each set are connected directly to each other, but this need not be the case. In other embodiments, fewer than four sets may be provided, or more than four sets may be provided.

In the embodiment of FIG. 7, each of the four sets of elements 12 is separated from each of the two circumferentially neighbouring sets by a set of the circumferentially deformable elements 14. Broken-line box 20 contains elements 14 in one of these sets. Four such sets of elements 14 are present in this embodiment, so as to provide a circumferentially alternating sequence of elements (alternating between the elements 12 and the elements 14). However other arrangements are possible. Four example fewer than four sets of elements 14 may be provided, or more than four sets of elements 14 may be provided. Different circumferential sequences may be provided.

Figure 8:
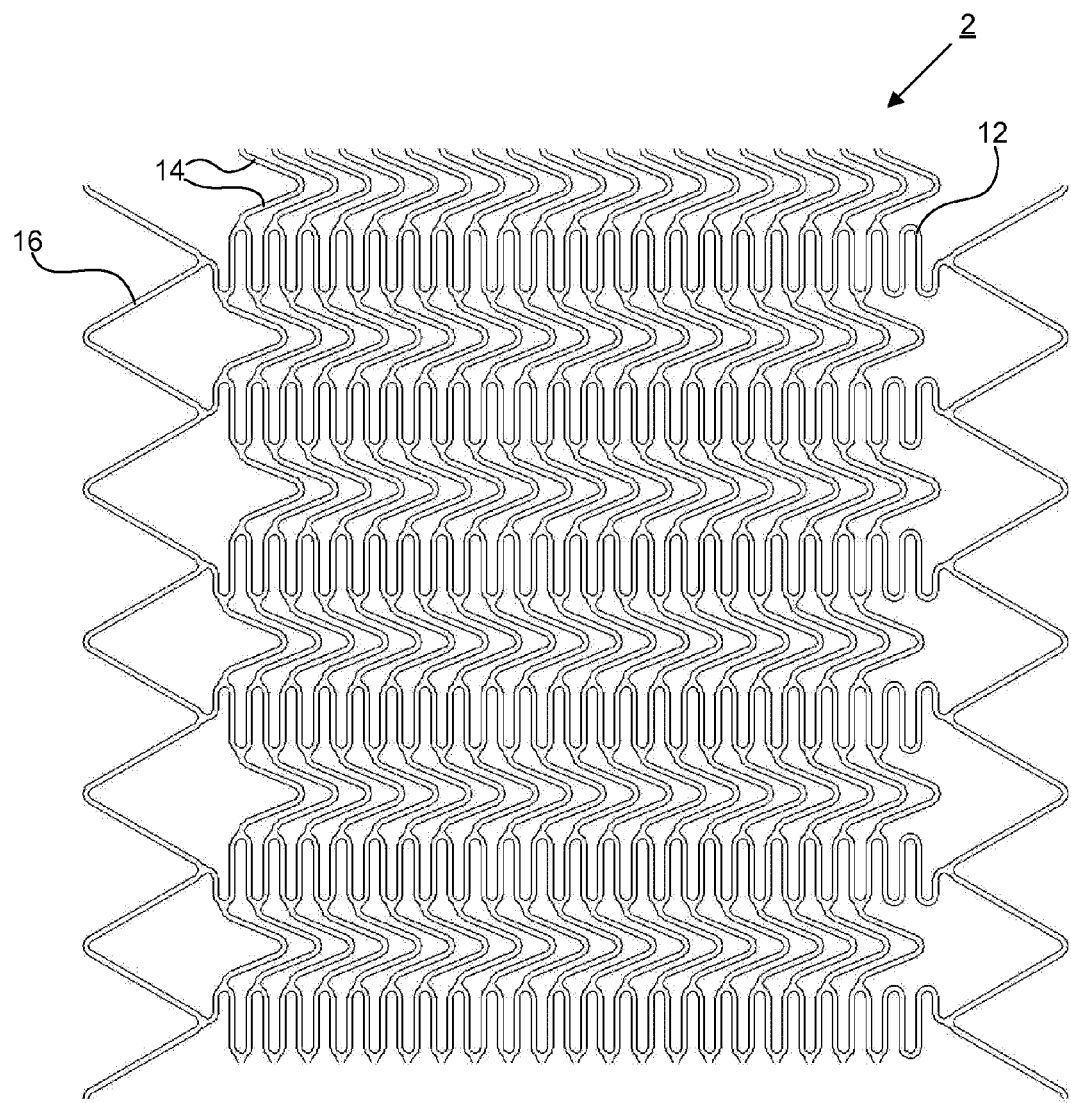
FIG. 8 depicts a variation of the arrangement shown in FIG. 7 in which six sets of longitudinally deformable elements are provided.

FIG. 8 shows an example of a frame 2 having six sets of the longitudinally deformable elements 12 and six sets of the circumferentially deformable elements 14. In general, reducing the number of sets of circumferentially deformable elements 14 will tend to increase longitudinal flexibility. On the other hand, having a larger number of sets of elements may limit the extent to which the frame 2 can be elongated and thus the extent to which the frame can be radially contracted for a given porosity in the fully radially expanded state.

Figure 9:
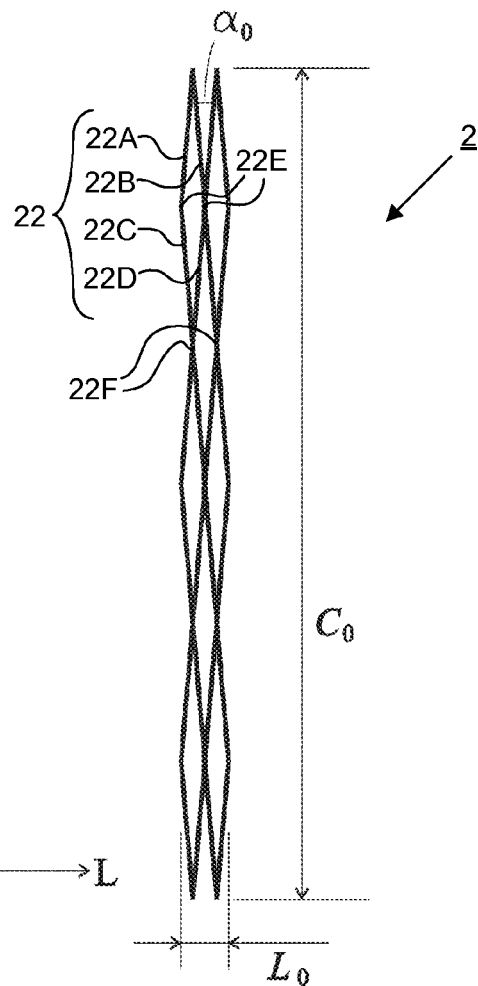
FIG. 9 is a schematic unfolded view of a portion of a network of interconnecting arms defining deformable elements that can each be deformed both longitudinally and circumferentially, the portion of a network being such as to form a portion of a stent in the fully radially expanded state when folded into the form of a cylinder.
Figure 10:
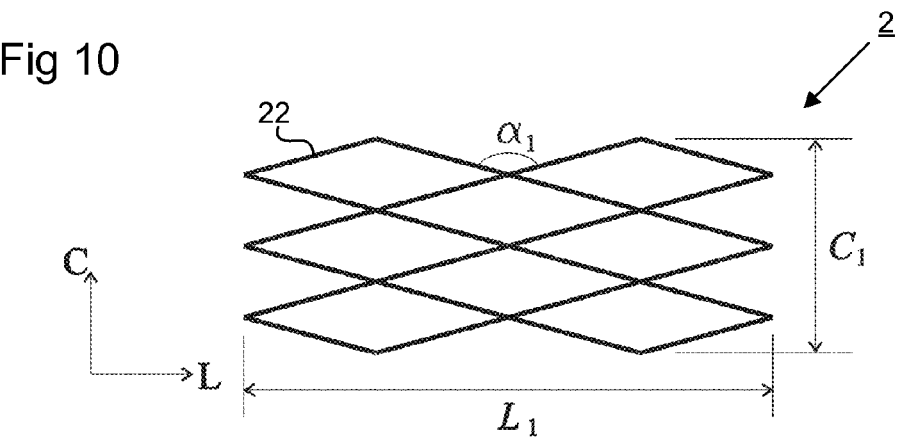
FIG. 10 is a schematic unfolded view of the network of FIG. 9 after extension in the longitudinal direction and compression in the circumferential direction.

FIGS. 9 and 10 illustrate schematically the geometry of an embodiment comprising a plurality of deformable elements 22 that provide both longitudinal and circumferential extension (and contraction). In an embodiment, a plurality of such deformable elements 22 together provide all (or a majority of) the longitudinal extension/contraction and circumferential extension/contraction of the frame 2. Each deformable element 22 may be considered as made up of four elements 22A, 22B, 22C and 22D connected together at four elbows to form a closed shape, for example a diamond shape. Longitudinal extension and circumferential contraction of the element 22 are achieved by reducing the angle at the elbows 22E. Longitudinal contraction and circumferential extension of the element 22 are achieved by increasing the angle at the elbows 22F.

In the embodiment shown, the elements 22 are connected directly to each other both longitudinally and circumferentially. In the embodiment shown, the elements 22 are configured to form a lattice having a constant spatial period both longitudinally and circumferentially. However this is not essential. The elements 22 may be configured to form a lattice that has a constant periodicity in the circumferential direction but a varying periodicity in the longitudinal direction. Alternatively, the elements 22 may be configured to form a lattice that has a constant periodicity in the longitudinal direction but a varying periodicity in the circumferential direction. Such arrangements make it possible to vary the porosity of the frame 2 as a function of position, for example so as to make a central region have lower porosity than more peripheral regions.

As with the embodiment of FIGS. 4 to 6, it is expected that in practice the sharp elbows would be provided in a more rounded form to avoid stresses and potential damage/irritation to tissue.

The deformable elements 22 may be referred to as longitudinally deformable elements that are capable of supporting circumferential extension, or as circumferentially deformable elements that are capable of supporting longitudinal extension.

In general, a longitudinal extension of the deformable element 22 will be accompanied by a circumferential contraction of the element 22 and vice versa.

FIGS. 9 and 10 show a structure comprising six deformable elements 22 (as we have defined them): three longitudinal rows each comprises two elements 22. Other configurations are possible. For example, each element 22 may be constructed differently. More than two or fewer than two (e.g. one or half of one) element 22 may be provided in each row. More than three or fewer than three rows may be provided.

The lattice structure shown in FIGS. 9 and 10 can be characterized by reference to an angle $\alpha_1$ by analogy with the arrangements depicted in FIG. 4 to 6. The frame 2 of FIGS. 9 and 10 may be seen as a variation of the embodiment of FIGS. 4 to 6 in which the circumferentially deformable elements 14 are omitted, such that circumferentially neighbouring sets of longitudinally aligned longitudinally deformable elements 12 are connected to each other directly (rather than via the circumferentially deformable elements 14).

Figure 11:
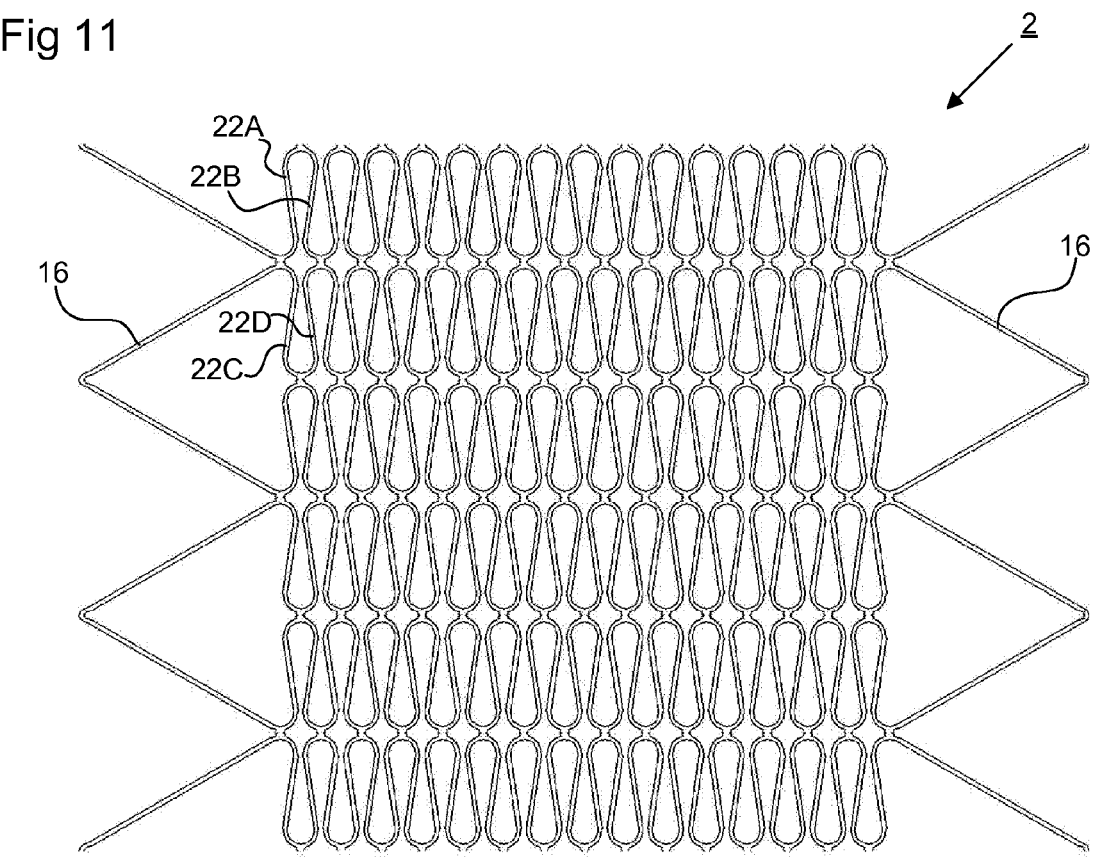
FIG. 11 is a schematic unfolded view of a network comprising six longitudinal rows of elements that can be deformed both longitudinally and circumferentially.

FIG. 11 shows an example of a frame 2 comprising seven units of the type illustrated in FIGS. 9 and 10, connected to each other in a longitudinal direction. The arms 22A, 22B, 22C, 22D making up each deformable element 22 are rounded rather than straight to avoid sharp angles. As in the embodiments of FIGS. 7 and 8 a zigzag ring 16 is provided at each end of the frame 2.

Figure 12:
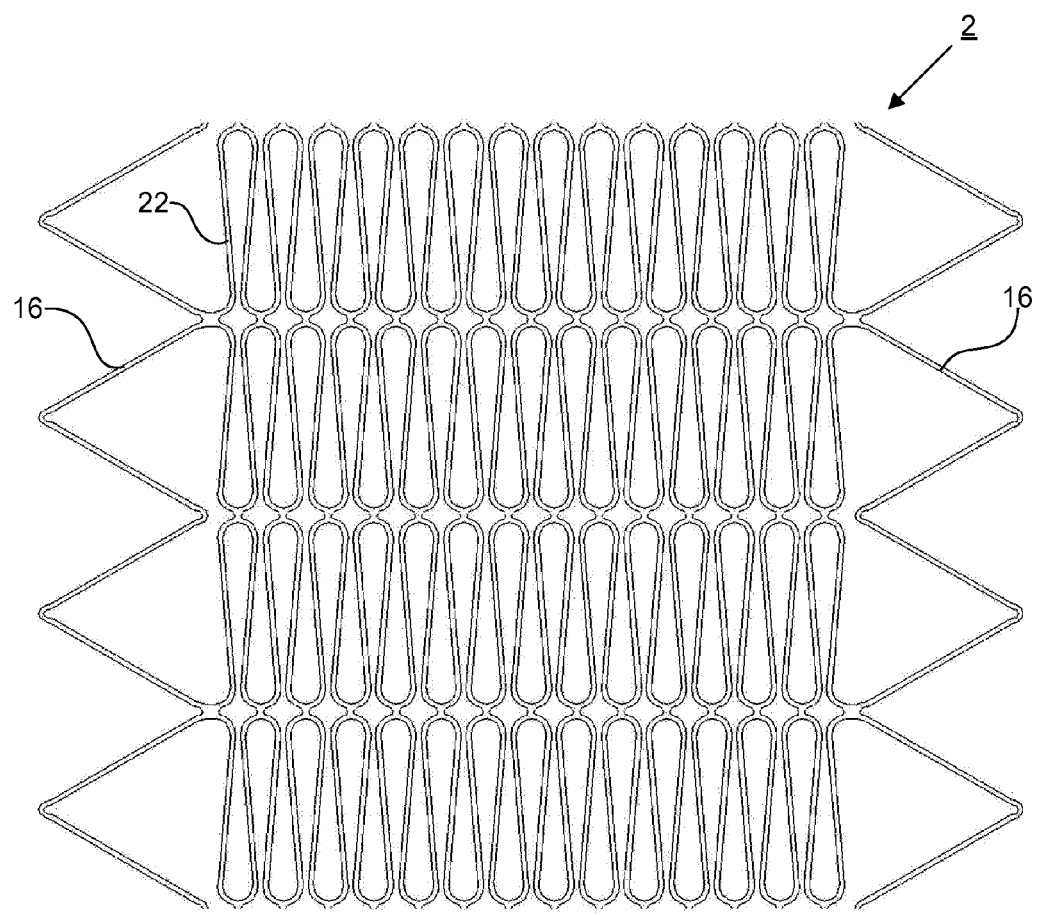
FIG. 12 is a schematic unfolded view of a variation of the network of FIG. 11 comprising four longitudinal rows of elements that can be deformed both longitudinally and circumferentially.

FIG. 12 shows an example of a frame 2 comprising two deformable elements in the circumferential direction rather than three (as in the embodiment of FIG. 11). However, the flow-diverter can have any number of deformable elements 22 in the circumferential direction. In general, the greater the number of deformable elements 22 in the circumferential direction the lower the flexibility of the frame 2. On the other hand, increasing the number of elements will tend to reduce the extent to which the frame 2 can be lengthened and thus limit the degree to which the frame 2 can be radially contracted for a given porosity in the fully radially expanded state.

In the embodiments shown in FIGS. 4 to 12, the frame 2 is constructed so as to have a constant porosity both longitudinally and circumferentially. This may be achieved by arranging for all of the longitudinally deformable elements 12 to be identical and for all of the circumferentially deformable elements 14 to be identical, for example, at all positions of the frame 2. In embodiments where the frame 2 comprises just one type of element 22 that accommodates both the longitudinal and radial extension/contraction, all of the elements 22 may be provided in identical form at all positions on the frame 2. In these arrangements, the porosity of the frame 2 is thus constant as a function of position (at the resolution of individual deformable elements 12, 14, 22). However, this is not essential. The nature of the deformable elements 12, 14, 22 can be varied as a function of position to provide a porosity that varies as a function of position. The porosity may be made to vary as a function of position in the longitudinal direction, in the circumferential direction, or both.

Figure 13:
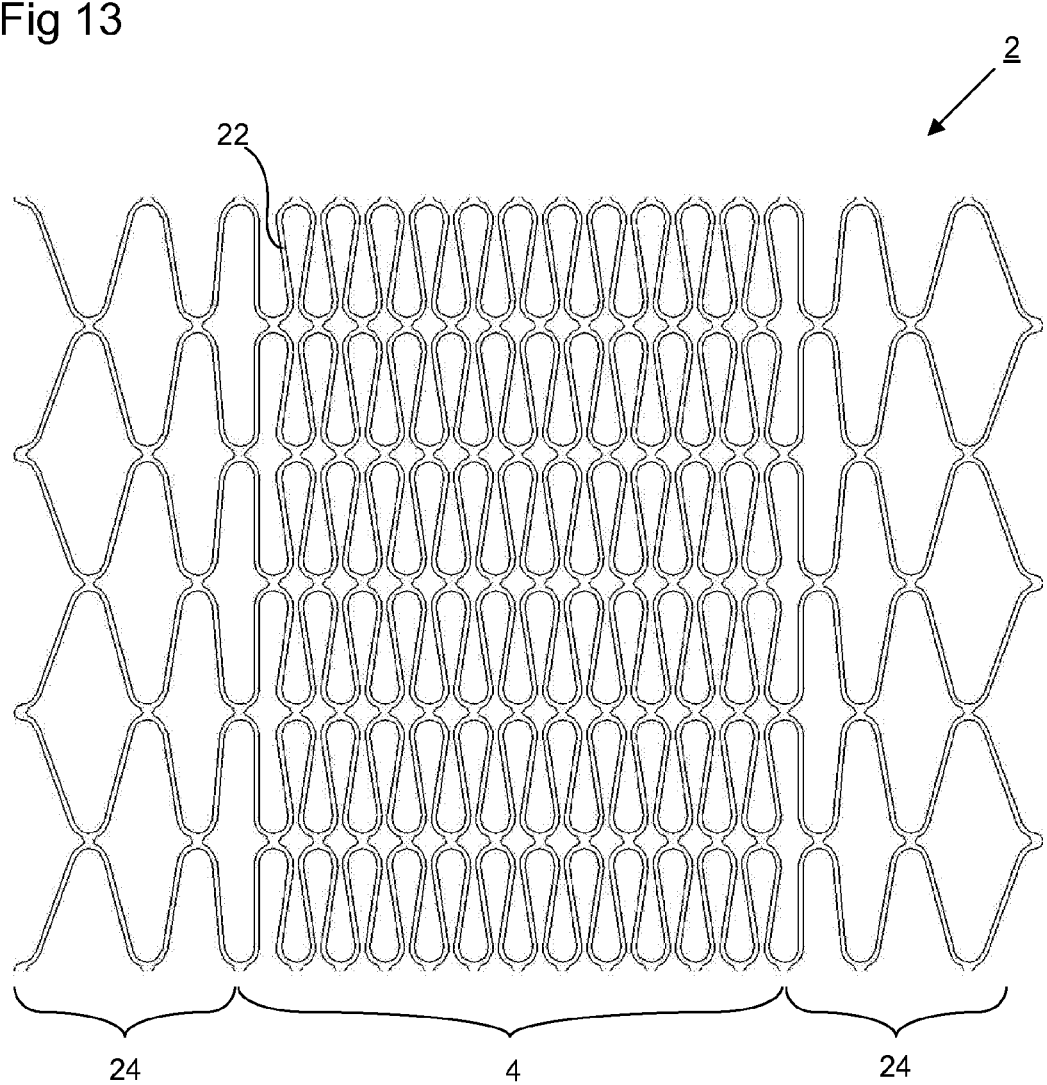
FIG. 13 is a schematic unfolded view of a network having a low porosity region that is longitudinally surrounded by higher porosity regions formed by higher porosity versions of the elements forming the low porosity region.

FIG. 13 depicts an example arrangement of the type shown in FIGS. 9 to 12 except the deformable elements 22 are configured to have a porosity that varies in the longitudinal direction. In a central region, which may correspond to the low porosity region 4 of the frame 2, the deformable elements 22 are relatively closely spaced and have a low porosity. In longitudinally peripheral regions 24, the deformable elements 22 are configured to be less closely spaced, thus providing a higher porosity. In other embodiments, the deformable elements 22 could be arranged to have porosity that varies in the circumferential direction also. For example, the arrangement of FIG. 13 could be adapted so that the low porosity region 4 is surrounded on the top and bottom sides also by a higher porosity region. The ability to vary the porosity in this way provides useful design flexibility. For example, it allows the low porosity region 4 to be made smaller so as to target the neck of the aneurysmal sac more precisely. In this way it is possible to avoid unnecessarily positioning low porosity portions of the frame 2 against regions of tissue that are not associated with the aneurysm. Low porosity regions of the frame 2 will tend to be stiffer and more likely to cause irritation or damage to tissue. They may exert a larger radial force against tissue for example. The stiffness may also disadvantageously limit the extent to which the frame 2 can conform well with tortuous regions of vasculature, so it may be desirable to minimise the size of the low porosity region 4 for this reason also. Alternatively or additionally, the opening to the aneurysmal sac may be located in close proximity to one or more other openings (e.g. branch blood vessels) which should not be blocked. Controlling the size and shape of the low porosity region 4 in the way described makes it possible to tailor the frame 2 so that the low porosity region 4 of the stent is positioned over the opening the aneurysmal sac while neighbouring openings are covered only (or mainly) by higher porosity regions of the frame 2.

The frame 2 may be manufactured from a sheet of material from which the structures described above are cut. The cutting may be performed, for example and without limitation, by laser cutting which can provide the desired accuracy in a straightforward manner. The cutting is performed to produce the frame 2 in its fully radially expanded (unconstrained) state. The frame 2 may be polished after the cutting to remove sharp edges, which may assist with inserting the frame into a delivery catheter for example and/or reduce the chances of irritation or injury to a patient.

The sheet of material may initially be formed as a tube, for example by extrusion. In this case, the cutting is performed directly on the tube. Alternatively, the sheet of material may initially be formed as a flat sheet, which is subsequently curved into a tube and joined along the facing edges, for example by laser welding. In this case, the cutting may be performed on the flat sheet before joining or on the joined tube. When performed on the flat sheet before joining, the cutting may be performed, for example and without limitation, by chemical etching.

The material of the sheet may in general be any biocompatible material, for example a metal, for example 316L stainless steel. Generally, a biocompatible material is selected with appropriate mechanical properties for the site at which the frame 2 is to be used. The sheet may be a unitary piece of material or a multi-layer material. The sheet may or may not be coated with a substance for adapting the physical properties of the frame 2 and/or with a medicament which the frame 2 thus delivers.

One advantageous type of material is a superelastic material, for example a shape memory alloy, for example Nitinol. The use of a superelastic material has the advantage that the frame 2 may be self-expanding in situ. In particular, the material is selected so that it is in the superelastic state at the temperature in situ (body temperature).

As described above the frame 2 may consists of a network of interconnecting arms. The interconnecting arms may be formed by cutting out the material in between the arms, using a laser for example. The network of interconnected arms may be cut from a cylindrical tube for example. All of the interconnected arms may lie at a common radius, so as to form a cylinder. When viewed longitudinally the frame 2 cross-section may appear circular. This configuration may persist for all configurations of the frame 2 that are expected in normal use, from the fully expanded state to the maximally radially contracted state. The maximally radially contracted state may be defined as the state in which any further radial contraction of the frame 2 would involve buckling of the frame (i.e. loss of the cylindrical shape), for example a caving in of a side of the cylinder. Generally the maximally radially contracted state will correspond to a state which has very low or zero porosity, where all or a very large proportion of the interconnected arms are very close to or in contact with neighbouring arms at points other than the points of connection between the arms, for example along their length.

The frame 2 may be inserted into the region to be treated using a delivery catheter. The delivery catheter may comprise a narrow tube, for example. The inner diameter of the part of the delivery catheter that will receive the frame 2 may be less than 5 mm, or less than 3 mm, so that the radius of the frame in the radially contracted state will need to be less then 2.5 mm or less than 1.5 mm respectively. It is desirable to make the delivery catheter as narrow as possible to facilitate the insertion process and minimize the risk of irritation or injury to the patient. Thinner delivery catheters may be able to access regions that thicker delivery catheters cannot.

Insertion of a frame into the delivery catheter could be difficult to achieve efficiently and reproducibly due to the small dimension involved. Described below are two example approaches for inserting the frame which address this challenge.

In a first embodiment the frame is formed from a material that undergoes a temperature induced phase transition from a state in which it can be deformed plastically and a state in which it is elastic. An example of such a material is Nitinol which adopts a highly elastic austenite phase at body temperature and a weaker, plastically deformable martensite phase at lower temperatures.

A frame formed from such a material can be cooled to a temperature at which the deformation is predominantly plastic, elongated and radially contracted to form the radially contracted state while still cold, and then inserted into the delivery catheter. The cooling can be carried out by immersing the frame in a bath of liquid alcohol for example. When the frame is warmed back up to room temperature or body temperature it will become elastic again but is restrained by the interior walls of the delivery catheter until the frame is to be deployed. When the frame is to be deployed, it is pushed out of the delivery catheter. As the frame leaves the delivery catheter it will spring open elastically into a radially expanded state with the frame, to press outwards against the walls of the blood vessel, with the low porosity region of the frame spanning the opening to an aneurysm for example. This approach for inserting the frame into the delivery catheter is convenient because it is easier to manipulate the frame in the plastic state than in the elastic state. In the plastic state the elongation and radial compression operations can be carried out separately from the act of inserting the frame into the delivery catheter.

In a second embodiment, an arrangement is provided which allows the frame to be inserted into the delivery catheter in a single pushing action. The use of a single pushing action makes it possible to insert the frame into the delivery catheter efficiently and reliably without first having to cool the frame down to a plastic state.

Figure 14:
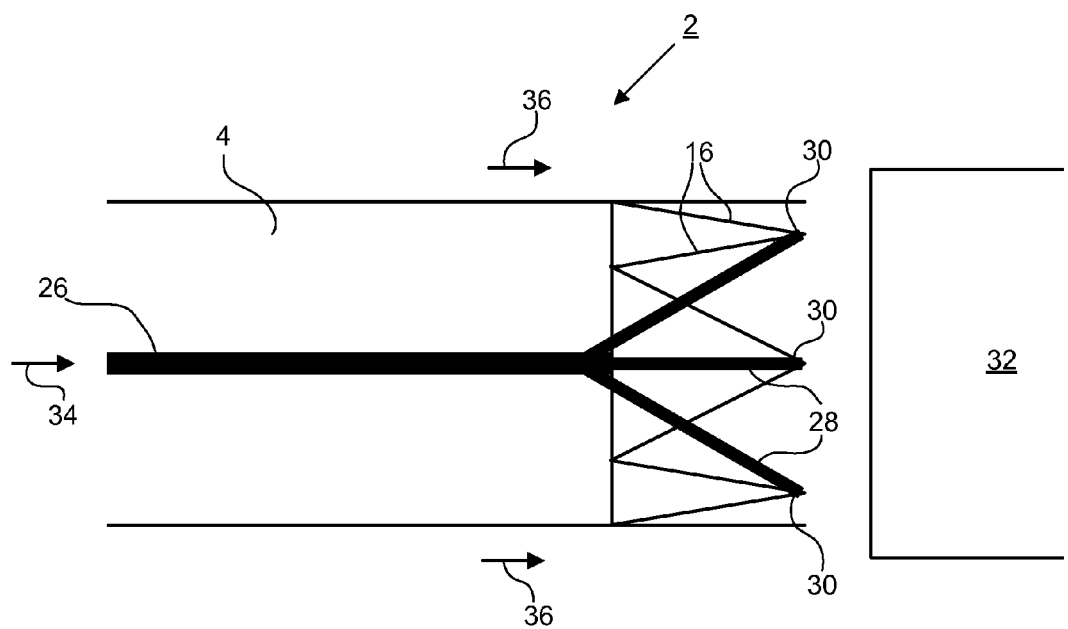
FIG. 14 is a schematic illustration of a longitudinally rigid element being used to assist with insertion of a stent for insertion into a delivery catheter.

An example configuration is depicted schematically in FIG. 14. The left part of the figure depicts a leading end of a frame 2 and the right part of the figure depicts a facing end of a delivery catheter 32 into which the frame 2 is to be inserted. The direction of insertion is shown by arrows 36. The low porosity region 4 is not shown in detail. The leading edge of the frame 2 is adapted so as to present one or more anchoring points 30. For example, the leading edge of the frame 2 may be provided with a zigzag structure 16 having elbows pointing longitudinally forwards. The anchoring points 30 allow for engagement with a longitudinally rigid element 26. In the example shown, the engagement between the anchoring points 30 and the element 26 are provided by means of laterally spreading arms 28. In the example shown the laterally spreading arms 28 comprise hooks or similar that allow engagement with the elbows of the zigzag elements 16. In other embodiments the engagement between the element 26 and the frame 2 might be realized in different ways. In general, any engagement that is capable of transmitting a longitudinal force applied to the element 26 (see arrow 34) to the leading edge of the frame 2 may be used.

The insertion process may proceed as follows. An end of the frame 2 opposite to the leading end of the frame 2 (depicted) is secured longitudinally. The longitudinally rigid element 26 is then inserted into the frame 2 from the end of the frame 2 opposite to the leading end of the frame and pushed through until the element engages with the leading end of the frame 2 (for example by means of anchoring points 30). The rigid element 26 is then forced further forwards. The force is transmitted to the frame 2 and the frame is made to elongate. Depending on the particular structure of the frame 2, the force of elongation may cause a simultaneous radially contraction, such that the frame 2 eventually adopts a radially contracted state that is sufficiently narrow to fit into the delivery catheter without any separate force needed radially. If a separate radially inwards force is needed to provide the radial contraction, this can be provided separately (e.g. by manual compression) or a structure such as a funnel positioned in the delivery catheter 32 can be used to assist.

Insertion of the stent into the delivery catheter may be further facilitated by lubricating the frame 2 and/or by polishing the frame 2 to make the outer surface of the frame 2 smoother.

It is to be understood that where reference is made to a stent comprising a frame, this is to include a stent that consists of the frame (i.e. with no other elements) and a stent that consists of the frame and other additional elements.

The invention claimed is:

1. A stent for redirecting blood flow away from an aneurysmal sac, comprising:
    an elongate frame that is radially contractable from a fully radially expanded state to a radially contracted state in a process involving elongation of the frame, wherein:
    the fully radially expanded state represents the state of the frame at body temperature when no external force is applied to the frame;
    in the radially contracted state the frame has a maximum lateral dimension that is at least 30% smaller than the maximum lateral dimension of the frame in the fully radially expanded state;
    the frame comprises a low porosity region for positioning at the opening to the aneurysmal sac, the low porosity region having a porosity of less than 50% when the frame is in the fully radially expanded state, wherein:
    the frame comprises a network of interconnecting arms;
    all of the interconnecting arms are configured to remain at a common radius, with no overlap in the radial direction, for all possible radially contracted states that do not involve buckling of the frame;
    the frame comprises a plurality of longitudinally deformable elements for providing elongation of the frame and a plurality of circumferentially deformable elements for providing radial contraction of the frame; and
    one or more of the longitudinally deformable elements can be expanded or contracted without any change in the shape of one or more of the circumferentially deformable elements.

2. A stent according to claim 1, wherein:
    the elongation of the frame between the fully radially expanded state and the radially contracted state is at least 25%.

3. A stent according to claim 1, wherein the frame is cylindrical in the fully radially expanded state, in the radially contracted state, or both.

4. A stent according to claim 1, wherein:
    the maximum lateral dimension of the frame in the radially contracted state is smaller than 5 mm.

5. A stent according to claim 1, wherein:
    the maximum lateral dimension of the frame in the radially contracted state is at least 50% smaller than the maximum lateral dimension of the frame in the fully radially expanded state.

6. A stent according to claim 1, wherein:
    expansion or contraction of one or more of the longitudinally deformable elements causes a change in shape of one or more of the circumferentially deformable elements.

7. A stent according to claim 1, wherein the plurality of longitudinally deformable elements comprises a set of longitudinally deformable elements that are connected together, directly or indirectly, so as to act in series longitudinally, wherein the plurality of longitudinally deformable elements comprises a plurality of said sets of longitudinally deformable elements connected in series, each said set being positioned at a different circumferential position, and wherein the longitudinally deformable elements in at least one of said sets of longitudinally deformable elements arranged in series are connected together to form a longitudinally periodic structure.

8. A stent according to claim 1, wherein:
    the plurality of circumferentially deformable elements are distinct from the plurality of longitudinally deformable elements.

9. A stent according to claim 1, wherein said plurality of circumferentially deformable elements comprises a first circumferentially deformable element and second circumferentially deformable element, at least part of the first circumferentially deformable element being bounded on one or both sides in the circumferential direction by a portion of the second circumferentially deformable element when the frame is in the fully radially expanded state, wherein the frame is configured so that the first and second circumferentially deformable elements move further apart longitudinally on elongation of the frame.

10. A stent according to claim 9, wherein the frame is configured so that no portion of the first circumferentially deformable element is bounded on either side in the circumferential direction by any portion of the second circumferentially deformable element when the frame is in the radially contracted state.

11. A stent according to claim 9, wherein the first circumferentially deformable element is connected directly to a first longitudinally deformable element and the second circumferentially deformable element is connected directly to a second longitudinally deformable element, the first longitudinally deformable element being at a different longitudinal position to the second longitudinally deformable element, and wherein the first and second longitudinally deformable elements are connected together so as to act in series, elongation of the frame causing the separation between the first and second longitudinally deformable elements, and between the first and second circumferentially deformable elements attached thereto, to increase.

12. A stent according to claim 1, wherein the plurality of circumferentially deformable elements comprises a set of circumferentially deformable elements that are connected together, directly or indirectly, so as to act in series circumferentially, wherein the plurality of circumferentially deformable elements comprises a plurality of said sets of circumferentially deformable elements connected to act in series, each said set being positioned at a different longitudinal position, and wherein the circumferentially deformable elements in at least one of said sets of circumferentially deformable elements arranged in series are connected together so as to form a circumferentially periodic structure.

13. A stent according to claim 1, wherein the deformation of the longitudinally deformable elements and of the circumferentially deformable elements is elastic at body temperature, for all degrees of radial contraction between the fully radially expanded state and the radially contracted state.

14. A stent according to claim 1, wherein the frame comprises a plurality of longitudinally or circumferentially deformable elements that have different porosities when the frame is in the fully radially expanded state, wherein the average porosity of said plurality of longitudinally or circumferentially deformable elements having different porosities is greater in a longitudinally central region of said low porosity region of the frame than in a longitudinally peripheral region of said low porosity region of the frame, when the frame is in the fully radially expanded state.

15. A stent according to claim 14, wherein:
the average porosity of said plurality of longitudinally or circumferentially deformable elements having different porosities is greater in a selected circumferential region of said low porosity region of the frame than in other circumferential regions of said low porosity region of the frame, at least when the frame is in the fully radially expanded state.

16. A stent according to claim 1, wherein:
the frame is formed from Nitinol or stainless steel and the frame is formed by laser cutting of a hollow tube.

* * * * *